United States Patent [19]

Rauchschwalbe et al.

[11] 4,339,396
[45] Jul. 13, 1982

[54] PROCESS FOR THE PREPARATION OF NAPHTHALENESULPHONYL CHLORIDE

[75] Inventors: Günter Rauchschwalbe, Cologne; Karl Mannes; Dietmar Mayer, both of Leverkusen, all of Fed. Rep. of Germany

[73] Assignee: Bayer Aktiengesellschaft, Leverkusen, Fed. Rep. of Germany

[21] Appl. No.: 163,357

[22] Filed: Jun. 26, 1980

[30] Foreign Application Priority Data

Jul. 17, 1979 [DE] Fed. Rep. of Germany ....... 2928744

[51] Int. Cl.³ ............................................ C07C 143/30
[52] U.S. Cl. ................................................. 260/543 R
[58] Field of Search ...................................... 260/543 R

[56] References Cited

FOREIGN PATENT DOCUMENTS 1963383  8/1970  Fed. Rep. of Germany .

OTHER PUBLICATIONS

HELVETICA CHIMICA ACTA, Band 52 No. 5, 1959–H. H. Bosshard et al, "Eine Methode zur katalysierten Herstellung von Carbonsäure' und Sulfosäure-chloriden mit Thionylchlorid"-pp. 1653 to 1658 *p.1654*.

SYNTHESIS, Band 1974, A. BARCO et al, "A New Preparation of Sulfonyl Chlorides via Pyridinium Sulfonates"-p. 877.

*Primary Examiner*—Robert Gerstl
*Assistant Examiner*—Frederick W. Pepper
*Attorney, Agent, or Firm*—Sprung, Horn, Kramer & Woods

[57] ABSTRACT

In a process for the preparation of a naphthalenesulphonyl chloride by reacting an alkali metal salt or ammonium salt of a naphthalenesulphonic acid with thionyl chloride in the presence of a catalytically active substance the improvement wherein the reaction is carried out in the presence of an optionally substituted pyridine, tertiary aliphatic amine, secondary amidine and/or quaternary ammonium salt.

11 Claims, No Drawings

PROCESS FOR THE PREPARATION OF NAPHTHALENESULPHONYL CHLORIDE

The invention relates to a process for the preparation of naphthalenesulphonyl chlorides by reacting alkali metal salts or ammonium salts of the corresponding naphthalenesulphonic acids with thionyl chloride in the presence of catalytically active substances and if appropriate in the presence of inert solvents or diluents.

It is known to prepare naphthalenesulphonyl chlorides from the corresponding sulphonic acids or alkali metal salts thereof and thionyl chloride in the presence of dialkylformamides, preferably dimethylformamide, as the catalyst and if appropriate in the presence of inert solvents (Helv. Chim. Acta 42, 1654 (1959)).

Although naphthalenesulphonyl chlorides can be prepared in good yields by this process, the use of dimethylformamide involves serious disadvantages. Thus, it has been found that dimethylcarbamoyl chloride, which exhibits a marked carcinogenic action in mice (compare C.A. 77, 97540 b) can be formed from dimethylformamide and thionyl chloride (compare C.A. 75, 48340 m).

It is furthermore known that pyridinium salts of sulphonic acids and thionyl chloride form sulphonyl chlorides in good yields (Synthesis 1974, 877). According to this literature reference, the pyridinium salt of the sulphonic acids is first prepared with excess base and is isolated and then reacted, in the crystalline form, with thionyl chloride.

However, the process has the disadvantage that the pyridinium salt of the sulphonic acid must first be isolated and purified, and an excess of pyridine is required for the preparation of the pyridinium salt. The process thus requires technical effort and becomes less economical.

A process has now been found for the preparation of naphthalenesulphonyl chlorides by reacting the alkali metal salts or ammonium salts of naphthalenesulphonic acids with thionyl chloride in the presence of catalytically active substances and if appropriate in the presence of inert solvents or diluents, which is characterised in that the reaction is carried out in the presence of optionally substituted pyridines, tertiary aliphatic amines, secondary amidines and/or quaternary ammonium salts.

Optionally substituted pyridines which can be employed in the process according to the invention are those of the general formula (I)

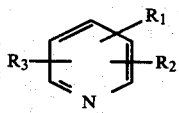

in which
R$_1$, R$_2$ and R$_3$ are identical or different and represent hydrogen, halogen, a hydroxyl, sulpho or cyano group or an alkyl, aryl, aralkyl, dialkylamino or N-pyridine radical,
or wherein
two of the radicals R$_1$ to R$_3$, if they are adjacent, represent a benzo radical.

Halogens which may be mentioned are: fluorine, chlorine, bromine and iodine, preferably chlorine and bromine.

Possible radicals R$_1$, R$_2$ and R$_3$ are, for example: alkyl radicals including cyclo and bicyclo alkyl radicals with up to 10 C atoms, preferably up to 5 C atoms, such as methyl, ethyl, n-propyl, iso-propyl, n-butyl, iso-butyl, tert.-butyl, n-pentyl, iso-pentyl, hexyl, octyl, decyl, cyclohexyl and decahydronaphthyl, most preferably methyl, ethyl and n-propyl; aryl radicals with up to 10 C atoms, preferably up to 6 C atoms, such as phenyl, tolyl and naphthyl, preferably phenyl and tolyl; aralkyl radicals with up to 14 C atoms, preferably up to 8 C atoms, such as benzyl, phenylethyl, phenylpropyl, phenylbutyl, dihydronaphthyl, tetrahydronaphthyl, naphthylmethyl and naphthylethyl, preferably benzyl and phenylethyl; dialkylamino radicals with up to 10 C atoms, preferably up to 6 C atoms, such as dimethyl-, diethyl-, dipropyl-, dibutyl-, diamyl-, ethylhexyl- and methylcyclohexyl-amino, pyrrolidino, piperidino, morpholino, preferably dimethylamino, pyrrolidino, piperidino and morpholino; and N-pyridino radicals with up to 12 C atoms, preferably up to 8 C atoms, such as N-pyridino, N-picolino, N-lutidino, N-collidino, N-(methylethylpyridino), N-quinolino and N-isoquinolino, preferably N-pyridino, N-picolino and N-lutidino.

Benzo radicals which may be mentioned are those with up to 10 C atoms, preferably up to 6 C atoms, such as benzo and naphtho, preferably benzo.

Optionally substituted pyridines which may be mentioned are, for example: pyridine, picoline, lutidine, collidine, methylethylridine, (N-pyridinio)-pyridine chloride, chloropyridine, cyanopyridine, hydroxypyridine, pyridinesulphonic acid, dimethylaminopyridine, morpholino-, pyrrolidino- and piperidino-pyridine, quinoline and isoquinoline, preferably pyridine, picoline, lutidine, 4-cyanopyridine, 4-dimethylaminopyridine and isoquinoline.

It is also possible, of course, to employ addition compounds of optionally substituted pyridine and thionyl chloride in the process according to the invention.

Tertiary aliphatic amines which can be employed in the process according to the invention are those of the general formula (II)

in which
R$_4$, R$_5$ and R$_6$ are identical or different and represent an alkyl, cycloalkyl, N-alkenylaldimino, N-alkenyltimino or N,N-dialkylaminoalkylene radical, or
two or three of the radicals together form a monocyclic or bicyclic ring system which has up to 10 C atoms, preferably up to 8 C atoms, and optionally contains one or more hetero-atoms.

Examples of possible radicals R$_4$, R$_5$ and R$_6$ are: alkyl radicals with up to 6 C atoms, preferably up to 3 C atoms, such as methyl, ethyl, propyl, n-butyl, isobutyl, tert.-butyl, pentyl and hexyl, preferably methyl and ethyl; cycloalkyl radicals with up to 10 C atoms, preferably up to 6 C atoms, such as cyclopentyl, cyclohexyl, methylcyclohexyl, cyclooctyl, cyclodecyl and decahydronaphthyl, preferably cyclohexyl; N-alkenylaldimino radicals with up to 15 C atoms, preferably up to 12 C atoms, such as 2-aza-buta-1,3-diene-1,4-diyl and 2-aza-pent-1-ene-1,5-diyl, preferably 2-aza-buta-1,3-diene-1,4-diyl; N-alkenylketimino radicals with up to 15 C atoms, preferably up to 12 C atoms, such as 1-methyl-2-aza-buta-1,3-diene-1,4-diyl, 1-butyl-2-aza-pent-1-ene-1,5-diyl, preferably 1-methyl-2-aza-buta-1,3-diene-1,4-diyl; and N,N-dialkylaminoalkylene radicals with up to 9 C atoms, preferably up to 4 C atoms, such as dimethylaminoethyl, diethylaminoethyl, dimethylaminopropyl and dimethylaminobutyl, preferably dimethylaminoethyl.

Examples which may be mentioned of monocyclic or bicyclic ring systems which optionally contain one or more hetero-atoms, such as oxygen, sulphur or nitrogen, are: pyrrolidine, piperidine, morpholine, diazabicyclo-octane, quinuclidine and 4-thiomorpholine, preferably pyrrolidine, piperidine and morpholine.

Tertiary aliphatic amines which may be mentioned are, for example: trimethylamine, triethylamine, N-methyl-pyrrolidine, N-methylmorpholine, N-methylpiperidine, tetramethylethylenediamine, bis-(2-dimethylaminoethyl)methylamine, 1,4-dimethylpiperazine, 1,4-diazabicyclo-octane, quinuclidine, 1,4,5,6-tetrahydro-1,2-dimethylpyrimidine, 1-methylimidazole, 1,2-dimethylimidazole, 1,5-diazabicyclo[4.3.0]-non-5-ene and 1,8-diaza-bicyclo[5.4.0]-undec-7-ene, preferably trimethylamine, triethylamine and N-methylpyrrolidine.

The tertiary aliphatic amines can, of course, also be employed in the process according to the invention in the form of their salts, such as hydrohalides, sulphates and phosphates.

Quaternary ammonium salts which can be employed in the process according to the invention are those of the general formula (III)

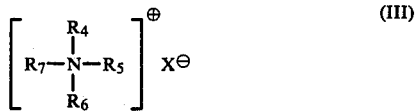
(III)

in which

R$^4$, R$^5$, R$^6$ and R$^7$ are identical or different and represent an alkyl, cycloalkyl, N-alkenylaldimino, N-alkenylketimino or N,N-dialkylaminoalkylene radical, or two or three of the radicals together form a monocyclic or bicyclic ring system which has up to 10 C atoms, preferably up to 8 C atoms, and optionally contains one or more hetero-atoms, and X$^\ominus$ represents chloride, bromide, iodide, sulphate, phosphate and bisulphate.

Quaternary ammonium salts which may be mentioned are, for example: tetramethylammonium chloride, tetraethylammonium chloride, N,N-dimethylpyrrolidinium bromide and hexaethylethylenediammonium chloride, preferably tetramethylammonium chloride and tetraethylammonium chloride.

Secondary amidines which can be employed in the process according to the invention are those of the general formula (IV)

$$R_8-NH-CH=N-R_9 \quad (IV)$$

in which R$_8$ and R$_9$ are identical or different and represent an alkyl or cycloalkyl radical or together form a monocyclic or bicyclic ring system with up to 15 C atoms, preferably up to 9 C atoms.

Examples of possible radicals R$_8$ and R$_9$ are: alkyl radicals with up to 10 C atoms, preferably up to 8 C atoms, such as methyl, ethyl, n-propyl, iso-propyl, n-butyl, iso-butyl, tert.-butyl, n-pentyl, iso-pentyl, hexyl and octyl, preferably methyl, ethyl and n-propyl; and cycloalkyl radicals with up to 10 C atoms, preferably up to 8 C atoms, such as cyclohexyl, methylcyclohexyl, cyclooctyl and cyclodecyl, preferably cyclohexyl.

Monocyclic or bicyclic ring systems according to the general formula (IV) which may be mentioned are: imidazole, hexahydrobenzimidazole and imidazoline, preferably imidazole.

Secondary amidines which may be mentioned are, for example: N,N'-dimethylformamidine, N-ethyl-N'-cyclohexyl-formamidine, imidazole, imidazoline and hexahydrobenzimidazole, preferably imidazole.

The optionally substituted pyridines, tertiary aliphatic amines, secondary amidines and/or quaternary ammonium salts can be employed in the process according to the invention in amounts of about 0.5 to about 10% by weight, preferably 2 to 5% by weight and particularly preferably 3 to 4% by weight, relative to the alkali metal salts or ammonium salts of the naphthalenesulphonic acid which are used.

Possible alkali metal salts of the naphthalenesulphonic acids are the lithium, sodium, potassium and/or rubidium salts, preferably the sodium or potassium salt.

Examples which may be mentioned of naphthalenesulphonic acids which can be employed, in the form of their alkali metal salts or ammonium salts, in the process according to the invention are: 1-naphthalenesulphonic acid, 2-naphthalenesulphonic acid, 1,4-, 1,5-, 1,6-, 2,6- and 2,7-naphthalenedisulphonic acid and naphthalene-1,3,6-trisulphonic acid, 1,3,5-trisulphonic acid and -1,3,7-trisulphonic acid, preferably 1-naphthalenesulphonic acid, 2-naphthalenesulphonic acid and 1,5-naphthalenedisulphonic acid.

In the process according to the invention, the alkali metal salts or ammonium salts of the naphthalenesulphonic acids are in general reacted with about the equivalent amount, preferably with 1.1 to 1.5 molar equivalents and particularly preferably with 1.2 to 1.3 molar equivalents, of thionyl chloride.

However, it is also possible to carry out the reaction of the naphthalenesulphonic acid salts with a larger excess of thionyl chloride, especially if the thionyl chloride is to assume the role of the suspending liquid reaction medium.

In this case, for example, about 1.5 to about 5 mols, preferably 2 to 3 mols, of thionyl chloride are employed per mol of sulphonate. When the reaction has ended, the excess thionyl chloride can be recovered and employed again in the reaction.

It is also possible to carry out the reaction according to the invention in the presence of inert solvents or diluents, in which case the abovementioned approximately equimolar amounts of thionyl chloride are sufficient.

Suitable solvents or diluents are, above all, compounds which are inert under the reaction conditions and are able to at least partly dissolve the naphthalenesulphonyl chloride formed.

Compounds which may be mentioned are, for example: aliphatic or aromatic hydrocarbons with up to 15 C atoms, preferably up to 8 C atoms, such as hexane, cyclohexane, toluene, xylene, octane, decalin, cumene, nesitylene and tetralin, preferably toluene, and halogenated aliphatic or aromatic hydrocarbons with up to 15 C atoms, preferably up to 8 C atoms, such as methylene chloride, chloroform, dichloroethane, trichloroethylene, tetrachloroethane, 1,1,2,3,3-pentachloropropane, hexachlorocyclopentadiene, octachlorocyclopentane, chlorobenzene, di- and tri-chlorobenzene, chlorotoluene and chloroxylene, preferably chlorobenzene.

The solvents or diluents can be employed individually or as mixtures with one another.

In general, the solvents or diluents are used in amounts of about ½ to about 5 liters per mol of sulphonate employed.

The process according to the invention can be carried out at temperatures in the range from about 20° to about 140° C., preferably at 50° to 130° C. and particularly preferably at 80° to 100° C.

Although the process according to the invention is preferably carried out under normal pressure, it is also possible to carry it out under increased pressure (up to about 50 bars).

In the process according to the invention, the thionyl chloride can be initially introduced into the reactin vessel and the sulphonate added or, vice versa, the sulphonate can be initially introduced and the thionyl chloride added.

The optionally substituted pyridines, tertiary aliphatic amines, secondary amidines and/or quaternary ammonium salts can be added to the reaction mixture before, during or after the addition of the second main component.

If the reaction is carried out in an inert solvent or diluent, it is advantageous to suspend the alkali metal salts or ammonium salts of the naphthalenesulphonic acids in the inert solvents or diluents and then to add the thionyl chloride and the optionally substituted pyridines, tertiary aliphatic amines, secondary amidines and/or quaternary ammonium salts.

When the reaction has ended, the inert solvent or diluent and/or excess thionyl chloride are distilled off, it being possible to employ both the inert solvent or diluent and the thionyl chloride again in the reaction.

The crude product which remains can be used as such directly, for example for the preparation of azo dyestuffs, as described in British Pat. Specification No. 634,488 or Swiss Patent Specification No. 261,840, or, if required by the further processing, it can be purified by distillation in vacuo or recrystallisation with suitable solvents.

The process according to the invention can be carried out either continuously or discontinuously.

The yields of naphthalenesulphonyl chlorides achieved by the process according to the invention are high; they are between about 80 and 100% of theory.

It is exceptionally surprising that the process according to the invention gives such good yields of naphthalenesulphonyl chlorides in a reaction which proceeds smoothly. In particular, it is known from Helv. Chim. Acta 42, 1654 (1959), that the reaction with thionyl chloride in the presence of pyridine as the catalyst is restricted to carboxylic acids.

The examples which follow are intended to illustrate the process according to the invention, but without restricting it to these examples.

EXAMPLE 1

104 g of sodium 2-naphthalenesulphonate are added slowly to a mixture, which has been warmed to 40° C. in an oil bath, of 100 ml of thionyl chloride and 3.0 g of pyridine.

The mixture is then warmed to the boiling point under reflux at an oil bath temperature of 100° C., for a further 1.5 hours, until the evolution of gas has ended, and is then subsequently stirred for a further 2 hours.

Excess thionyl chloride is distilled off. 130.3 g of crude product which contains 78.6% of 2-naphthalenesulphonyl chloride (aniline titration) are obtained, which corresponds to 99.9% yield, that is to say a quantitative yield within the scope of analytical tolerances.

Further examples with a corresponding experimental procedure may be shown in the form of a table.

TABLE

| Example | Amount of sodium 2-naphthalenesulphonate employed [mols] | Catalyst | Amount [% by weight] | Yield of naphthalene-2-sulphonyl chloride [%] |
|---|---|---|---|---|
| 2 | 2.3 | pyridine | 3 | 100 |
| 3 | 0.46 | 4-picoline | 3 | 98.7 |
| 4 | 0.46 | 4-cyanopyridine | 3 | 100 |
| 5 | 0.47 | 2-picoline | 3 | 91.3 |
| 6 | 0.46 | 4-(N,N-dimethylamino)-pyridine | 3 | 99.6 |
| 7 | 0.50 | isoquinoline | 6 | 100 |
| 8 | 0.46 | trimethylamine (as the hydrochloride) | 3 | 93.5 |
| 9 | 0.47 | triethylamine | 3 | 93.3 |
| 10 | 0.46 | N-methylpyrrolidine | 3 | 100 |
| 11 | 0.46 | imidazole | 3 | 96.9 |
| 12 | 0.46 | tetraethylammonium chloride | 3 | 82.0 |
| 13 | 0.46 | pyridine | 2 | 89.6 |
| 14 | 0.46 | pyridine | 4 | 99.3 |
| 15 | 0.46 | pyridine | 10 | 100 |

EXAMPLE 16

1 mol of sodium 2-naphthalenesulphonate and 7.0 g of pyridine are suspended in 600 ml of chlorobenzene and the suspension is warmed to 40° C. 143 g (1.2 mols) of thionyl chloride are added dropwise, whilst stirring, the mixture is warmed for a further 6 hours to 100° C. and the chlorobenzene and residual thionyl chloride are distilled off in vacuo.

The yield of naphthalenesulphonyl chloride is 99%.

EXAMPLE 17

115.1 g (0.5 mol) of sodium 1-naphthalenesulphonate are reacted as in Example 1; however, 6.0 g of pyridine are added and the mixture is stirred for a total of 3 hours. The yield was 146.4 g of crude product, which contained 76.8% of naphthalene-1-sulphonyl chloride (99.1% yield).

EXAMPLE 18

116.0 g (0.5 mol) of purified disodium naphthalene-1,5-disulphonate, 6 g of pyridine and 300 g of $SOCl_2$ were reacted with one another according to Example 1. Naphthalene-1,5-disulphonyl chloride which still contained about 28% of sodium chloride was obtained. The yield, according to the aniline titration method, was 90%.

EXAMPLE 19

The procedure followed is as described in Example 14, but the potassium salt of naphthalene-2-sulphonic acid is used. The yield was quantitative.

What is claimed is:

1. In a process for the preparation of a naphthalenesulphonyl chloride by reacting an alkali metal salt or ammonium salt of a naphthalenesulphonic acid with thionyl chloride in the presence of a catalytically active substance the improvement wherein the reaction is carried out in the presence of an optionally substituted pyridine, tertiary aliphatic amine, secondary amidine and/or quaternary ammonium salt, which is present in an amount of 0.5 to 10% by weight, based upon the weight of the alkali metal or ammonium salt of naphthalenesulphonic acid.

2. Process according to claim 1, wherein optionally substituted pyridine is employed of the formula (I)

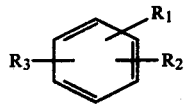

in which $R_1$, $R_2$ and $R_3$ are identical or different and represent hydrogen, halogen, a hydroxyl, sulpho or cyano group or an alkyl of up to 10 carbon atoms, aryl of up to 10 carbon atoms, aralkyl of up to 14 carbon atoms, dialkylamino with up to 10 carbon atoms or N-pyridine radical, or wherein two of the radicals $R_1$ to $R_3$, if they are adjacent, represent a benzo radical.

3. Process according to claim 1, wherein pyridine, picoline, lutidine, 4-dimethylamino-pyridine, 4-cyanopyridine or isoquinoline is employed as catalytically active substances.

4. Process according to claim 1, wherein a tertiary aliphatic amine is employed of the formula (II)

in which $R_4$, $R_5$ and $R_6$ are identical or different and represent an alkyl of up to 10 carbon atoms, cycloalkyl of up to 10 carbon atoms, N-alkenylaldimino with up to 15 carbon atoms, N-alkenylketimino with up to 15 carbon atoms, or N,N-dialkylaminoalkylene with up to 9 carbon atoms radical, or two or three of the radicals together form a monocyclic or bicyclic ring system which has up to 10 atoms and optionally contains one or more heteroatoms.

5. Process according to claim 1, wherein trimethylamine, triethylamine or N-methyl-pyrrolidine is employed as catalytically active substances.

6. Process according to claim 1, wherein a quaternary ammonium salt is employed of the formula (III)

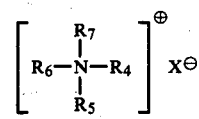

in which $R_4$, $R_5$, $R_6$ and $R_7$ are identical or different and represent an alkyl with up to 10 C atoms, cycloalkyl with up to 10 C atoms, N-alkenyladlimino with up to 15 C atoms, N-alkenylketimino with up to 15 C atoms or N,N-dialkylaminoalkylene with up to 9 C atoms radical, or two or three of the radicals together form a monocyclic or bicyclic ring system which has up to 10 C atoms and optionally contains one or more heteroatoms, and $X^\ominus$ represents chloride, bromide, iodide, sulphate, phosphate or bisulphate.

7. Process according to claim 1, wherein tetramethylammonium chloride or tetraethylammonium chloride is employed as catalytically active substances.

8. Process according to claim 1, wherein a secondary amidine is employed of the formula (IV)

$R_8-NH-CH=N-R_9$ in which $R_8$ and $R_9$ are identical or different and represent an alkyl with up to 10 C atoms or cycloalkyl with up to 10 C atoms radical or together form a monocyclic or bicyclic ring system with up to 15 C atoms.

9. Process according to claim 1, wherein imidazole is employed as catalytically active substance.

10. Process according to claim 1, wherein the reaction is conducted in the presence of an inert solvent or diluent.

11. A process according to claim 1, wherein the reaction is carried out in the presence of a substituted pyridine.

* * * * *